(12) United States Patent
Bai et al.

(10) Patent No.: US 11,041,179 B2
(45) Date of Patent: Jun. 22, 2021

(54) METHOD FOR PREPARING BRANCHED CYCLODEXTRIN AND APPLICATION THEREOF

(71) Applicant: Jiangnan University, Wuxi (CN)

(72) Inventors: Yuxiang Bai, Wuxi (CN); Zhengyu Jin, Wuxi (CN); Liuxi Xia, Wuxi (CN); Yun Wu, Wuxi (CN); Xueming Xu, Wuxi (CN); Zhengjun Xie, Wuxi (CN); Jinpeng Wang, Wuxi (CN); Xing Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/288,765

(22) Filed: Feb. 28, 2019

(65) Prior Publication Data
US 2019/0194708 A1    Jun. 27, 2019

Related U.S. Application Data

(63) Continuation of application No. PCT/CN2018/086869, filed on May 15, 2018.

(30) Foreign Application Priority Data

May 16, 2017   (CN) .......................... 2017103433501

(51) Int. Cl.
C12P 19/04 (2006.01)
C12P 19/18 (2006.01)
C12P 19/14 (2006.01)

(52) U.S. Cl.
CPC .............. C12P 19/04 (2013.01); C12P 19/14 (2013.01); C12P 19/18 (2013.01)

(58) Field of Classification Search
CPC ....................................................... C12N 9/18
See application file for complete search history.

(56) References Cited

FOREIGN PATENT DOCUMENTS

| CN | 103243140 A | 8/2013 |
|---|---|---|
| CN | 106967766 A | 7/2017 |
| CN | 107177647 A | 9/2017 |

OTHER PUBLICATIONS

L. Xia et al. "Efficient Synthesis of Glucosyl-β-Cyclodextrin from Maltodextrins by Combined Action of Cyclodextrin Glucosyltransferase and Amyloglucosidase", J. Agric. Food Chem 65:6023-6029 (Year: 2017).*

* cited by examiner

*Primary Examiner* — Rebecca E Prouty
(74) *Attorney, Agent, or Firm* — IPro, PLLC

(57) ABSTRACT

The disclosure herein relates to a method for preparing branched cyclodextrin and application thereof, and belongs to the technical field of synthesis of branched cyclodextrin. The method comprises the following steps: (1) dissolving maltodextrin in a phosphate buffer solution, and adding CGTase for reacting; (2) reducing enzyme activity by a physical method; and (3) adding a saccharifying enzyme to the reaction system of step (2), and performing high-temperature enzyme deactivation to obtain the branched cyclodextrin. The method has mild reaction conditions, and at the same time, cyclodextrin and unreacted substrates can be hydrolyzed via the weak coupling activity of CGTase, thereby realizing effective separation of the branched cyclodextrin.

14 Claims, 4 Drawing Sheets

METHOD FOR PREPARING BRANCHED CYCLODEXTRIN AND APPLICATION THEREOF

TECHNICAL FIELD

The disclosure herein relates to a method for preparing branched cyclodextrin and application thereof, and belongs to the technical field of synthesis of branched cyclodextrin.

BACKGROUND

Cyclodextrin, also known as cyclomalto-oligosaccharide, is a generic term for a class of oligosaccharides linked by a number of α-D glucopyranose units via α-1,4 glycosidic bonds. Cyclodextrin is severely restricted in application due to its poor water solubility, high hemolysis and nephrotoxicity, so modification of cyclodextrin is necessary.

Methods for modifying the cyclodextrin include a chemical method or a biological enzymatic method for modifying the cyclodextrin, in which certain specific substituents are grafted onto the cyclodextrin. Such a modified product obtained by introducing a substituent group while retaining a substantially unchanged cyclodextrin cavity structure is generally referred to as modified cyclodextrin, or modified cyclodextrin, or cyclodextrin derivative. When the substituent group is a glycosyl group, the glycosyl group is usually referred to as branched cyclodextrin such as glucosyl-cyclodextrin, maltosyl-cyclodextrin, galactosyl-cyclodextrin and mannose cyclodextrin.

Compared with cyclodextrin, branched cyclodextrin is widely used in food, pharmaceutical, chemical and cosmetic fields due to better water solubility, lower nephrotoxicity and lower hemolysis.

At present, there are two main methods for preparing branched cyclodextrin: one is to prepare branched cyclodextrin by using CGTase to act on starch or starch derivatives, and the branched cyclodextrin prepared by this method has low yield and low purity.

Another method is to prepare branched cyclodextrin by high-concentration cyclodextrin (α-cyclodextrin, β-cyclodextrin and γ-cyclodextrin) and maltose/maltotriose used as substrates under the action of pullulanase, and the remaining amount of cyclodextrin in the obtained mixture is relatively large; generally, the cyclodextrin is initially removed by crystallization, and then the branched cyclodextrin having higher purity is separated and obtained by column separation. The branched cyclodextrin-containing mixture prepared by the method still contains a large amount of cyclodextrin, the molecular weight of the cyclodextrin is close to that of the branched cyclodextrin and it is difficult to separate the branched cyclodextrin.

SUMMARY

In view of the above problems in the prior art, the applicant of the disclosure provides a method for preparing branched cyclodextrin by an enzymatic method. According to the method provided by the disclosure, firstly a mixture containing branched cyclodextrin, cyclodextrin and long-branched cyclodextrin is prepared from maltodextrin by utilizing the cyclization activity of cyclodextrin glycosyltransferase (CGTase for short) (or a branched cyclodextrin-containing mixture prepared by a pullulanase reverse synthesis method, or a mixture obtained by using α-galactosidase to act on cyclodextrin and melibiose is directly used), then, the activity of CGTase is controlled and the coupling effect of the CGTase is used to make the CGTase and the saccharifying enzyme according to 0.1-0.4 U/g of the mixture by dry weight act on the above mixture, only the branched cyclodextrin and glucose exist in the final target product, and the large molecular weight difference between the branched cyclodextrin and the glucose is favorable for subsequent separation and purification.

Furthermore, the method of the disclosure can be extended to a separation step of a method for preparing the branched cyclodextrin by pullulanase.

A first object of the disclosure is to provide a method of preparing branched cyclodextrin, the method comprising: treating a branched cyclodextrin-containing mixture with CGTase and a saccharifying enzyme, and the reaction time is 1-24 h, wherein the used amount of CGTase in the initial reaction system is controlled to be 0.1-0.4 U/g of the mixture by dry weight.

Optionally, the mixture is a mixture obtained by treating raw material, namely maltodextrin, with CGTase; or a branched cyclodextrin-containing mixture prepared by the pullulanase reverse synthesis method; or a mixture obtained by using α-galactosidase to act on cyclodextrin and melibiose.

In some embodiments, the branched cyclodextrin-containing mixture is specifically obtained by dissolving the raw material, namely maltodextrin, in a buffer solution, and adding the CGTase for reacting for 12-24 h.

In some embodiments, the buffer solution has a pH of 3.5-8.0, and optionally is a phosphate buffer solution.

In some embodiments, after the raw material, namely maltodextrin, is dissolved in the buffer solution, the mass concentration of the maltodextrin is 1-5%.

In some embodiments, the amount of the CGTase used is 0.3 U/g of the mixture by dry weight.

In some embodiments, the method specifically comprises:

(1) dissolving maltodextrin in a phosphate buffer solution, and adding the CGTase for reacting for 12-24 h to obtain a branched cyclodextrin-containing mixture;

(2) reducing CGTase activity by a physical method; and (3) adding a saccharifying enzyme to the reaction system of step (2) for reacting for 12-24 h and performing high-temperature enzyme deactivation to obtain the branched cyclodextrin.

In some embodiments, the physical method described in step (2) is 70-100° C. water bath heating.

In some embodiments, the method further comprises separation and purification of the reaction product after the saccharifying enzyme treatment reaction is completed.

In some embodiments, the separation and purification are carried out by liquid chromatography.

In some embodiments, the CGTase can be any one or more of α-CGTase, β-CGTase and γ-CGTase. After reacting with the α-CGTase, the β-CGTase and the γ-CGTase, the corresponding branched cyclodextrin target products include glucosyl-α-cyclodextrin, glucosyl-β-cyclodextrin and glucosyl-γ-cyclodextrin respectively.

In other embodiments, the branched cyclodextrin-containing mixture is a branched cyclodextrin-containing mixture prepared by the pullulanase reverse synthesis method.

In some embodiments, a mixture containing high-concentration cyclodextrin, maltose/maltotriose and a small amount of branched cyclodextrin is prepared by the pullulanase reverse synthesis method. The specific method is as follows: using high-concentration cyclodextrin and maltose/maltotriose as substrates, and preparing a mixture containing cyclodextrin, maltose/maltotriose and maltosyl/maltotriosyl-cyclodextrin under the action of pullulanase (for example, see Wang Shaojie, Jin Zhengyu. Study on the Process of Reverse Synthesis of Maltosyl β-CD by Pullulanase [J]. Science and Technology of Food Industry, 2005, 26(9): 105-107).

In some embodiments, the method comprises:

(a) dissolving the branched cyclodextrin-containing mixture powder prepared by the pullulanase reverse synthesis method in a buffer solution;

(b) placing the solution obtained in step (a) at 0-20° C. for crystallizing for 12-24 h (initially removing partial cyclodextrin in the mixture by cooling crystallization);

(c) centrifuging the solution obtained in step (b), and adding the supernatant to a pH 4.5-8.0 buffer solution to be fully dissolved; and (d) adding the CGTase and the saccharifying enzyme to the reaction system, and reacting at 45° C. for 1-10 h.

In some embodiments, the buffer solution in step (a) can be a pH 4.5 phosphate buffer solution.

In some embodiments, the amount of the CGTase added in step (d) is 0.1-0.4 U/g of the mixture by dry weight, optionally, 0.3 U/g of the mixture by dry weight.

In some embodiments, the method further comprises a step (e): separating and purifying the reaction product of step (d) by a membrane separation method to obtain single branched cyclodextrin.

In some embodiments, the branched cyclodextrin-containing mixture is a mixture obtained by using α-galactosidase to act on cyclodextrin and melibiose; glucosyl-cyclodextrin and galactosyl-cyclodextrin can be obtained respectively by adding the corresponding CGTase and saccharifying enzyme.

In some embodiments, the branched cyclodextrin-containing mixture is a mixture prepared by using the cyclodextrin and maltose as substrates by pullulanase; glucosyl-cyclodextrin and maltosyl-cyclodextrin can be obtained respectively by adding the corresponding CGTase and saccharifying enzyme.

The disclosure also claims the application of the above methods in the food, pharmaceutical, chemical and cosmetic fields.

Beneficial Effects:

(1) The branched cyclodextrin is prepared by using a two-step method and using maltodextrin as a starting material; firstly, a mixture containing cyclodextrin, branched cyclodextrin, long-branched cyclodextrin, etc. is prepared by using the cyclization activity of CGTase to act on the maltodextrin, then, the weak activity of the CGTase is compounded with the saccharifying enzyme to act on the above mixture, and the yield and purity of the obtained branched cyclodextrin are improved.

(2) The key step is to control the CGTase to be compounded with the saccharifying enzyme according to the amount of 0.1-0.4 U/g of the mixture by dry weight.

(3) When a small amount of CGTase and the saccharifying enzyme act together on the mixture containing cyclodextrin, branched cyclodextrin, long-branched cyclodextrin, etc., the saccharifying enzyme can hydrolyze the long-branched cyclodextrin into branched cyclodextrin, the coupling activity of the CGTase can selectively open the ring structure of cyclodextrin preferentially, and then the opened ring structure is hydrolyzed into glucose under the synergistic action of the saccharifying enzyme, thereby obtaining the branched cyclodextrin and glucose and facilitating subsequent separation and purification.

DETAILED DESCRIPTION

Example 1

Figure 1:
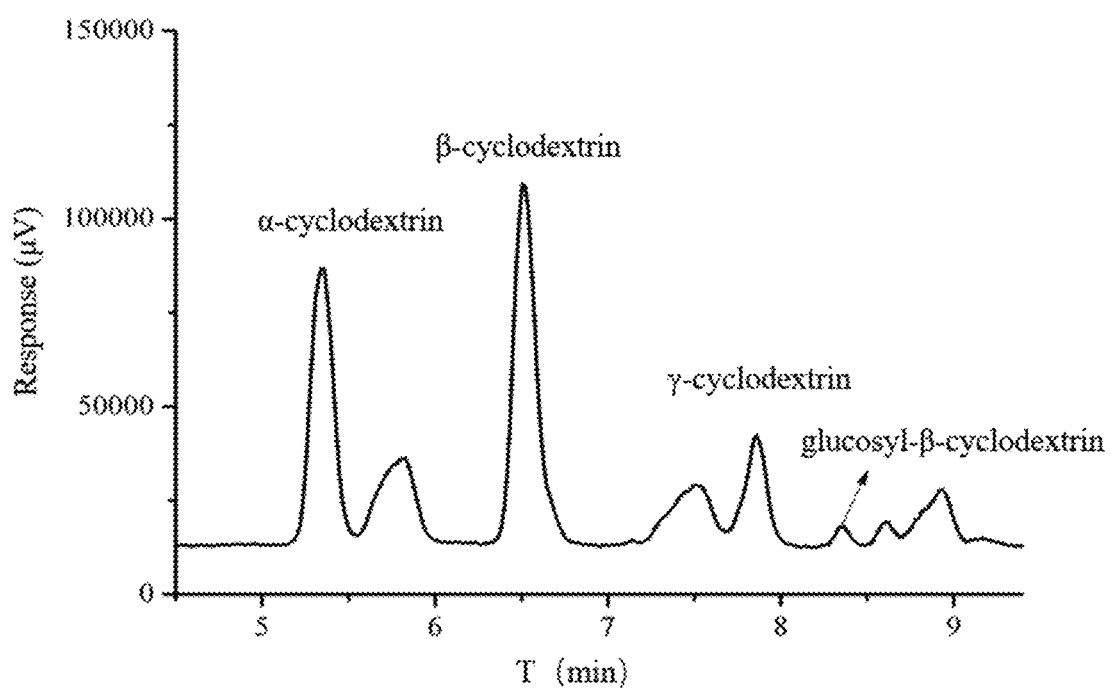
FIG. 1 is a high-performance liquid chromatogram of the product of step (1) in example 3 of the disclosure.

A method for preparing glucosyl-α-cyclodextrin by enzymatically treating maltodextrin, comprising the following specific steps:

(1) putting 10 mg of maltodextrin in a 2 mL centrifuge tube, adding 1 mL of a pH 4.5 (20 mM) phosphate buffer solution, and adding 0.36 U of α-CGTase, and reacting at 60° C. for 12 h to obtain a mixture containing branched cyclodextrin glucosyl-α-cyclodextrin;

(2) performing heating in water bath of 80° C. for 10 min, so as to enable the activity of the α-CGTase to be 0.003 U (i.e., to ensure that the initial activity of the α-CGTase in the subsequent reaction system is about 0.3 U/g of the mixture by dry weight);

(3) adding 0.72 U of saccharifying enzyme to the reaction system, reacting at 45° C. for 12 h, and insulating the temperature at 100° C. for 15 min to obtain a mixture containing glucosyl-α-cyclodextrin; and (4) separating and purifying the product obtained in step (3) by a high-performance liquid chromatography method to finally obtain 0.44 mg of glucosyl-α-cyclodextrin, wherein the proportion of the glucosyl-α-cyclodextrin to the main products (α-cyclodextrin, β-cyclodextrin, γ-cyclodextrin, and glucosyl-β-cyclodextrin) is 20%.

The high performance liquid chromatography conditions are listed as below: chromatograph: Shimadzu LC-20A; detector: differential detector; analytical column: APS-2 HYPERSIL column (250 mm*4.6 mm, 5 μm); mobile phase: acetonitrile:water=75:25 (v/v); column temperature: 30° C.; flow rate: 1 mL/min; injection volume: 200 μl.

Example 2

The inventors also attempted to prepare branched cyclodextrins by the following methods:

Option 1: Control of the CGTase activity in step (2) in the example 1 is omitted, that is, physical enzyme activity degradation treatment is not performed, the CGTase activity in the system is maintained at about 0.36 U, and other steps and parameters are the same as those in the example 1, specifically:

(1) putting 10 mg of maltodextrin in a 2 mL centrifuge tube, adding 1 mL of a pH 4.5 (20 mM) phosphate buffer solution, adding 0.36 U of α-CGTase, and reacting at 60° C. for 12 h to obtain a mixture containing branched cyclodextrin glucosyl-α-cyclodextrin; and (2) adding 0.72 U of saccharifying enzyme to the reaction system, reacting at 45° C. for 12 h, and insulating the temperature at 100° C. for 15 min to obtain a mixture containing glucosyl-α-cyclodextrin.

The results show that the percentage of the glucosyl-α-cyclodextrin in the mixture containing the glucosyl-α-cyclodextrin is 0%.

Option 2: The activity of the α-CGTase in step (2) in the example 1 is reduced to 0.006 U (i.e., to ensure that the initial activity of the α-CGTase in the subsequent reaction system is about 0.6 U/g of the mixture by dry weight); and other steps and parameters are the same as those in the example 1, specifically:

(1) putting 10 mg of maltodextrin in a 2 mL centrifuge tube, adding 1 mL of a pH 4.5 (20 mM) phosphate buffer solution, adding 0.36 U of α-CGTase, and reacting at 60° C. for 12 h to obtain a mixture containing branched cyclodextrin glucosyl-α-cyclodextrin;

(2) performing heating in water bath of 80° C. for 10 min, so as to enable the activity of the α-CGTase to be 0.006 U (i.e., to ensure that the initial activity of the α-CGTase in the subsequent reaction system is about 0.6 U/g of the mixture by dry weight); and (3) adding 0.72 U of saccharifying enzyme to the reaction system, reacting at 45° C. for 12 h, and insulating the temperature at 100° C. for 15 min to obtain a mixture containing glucosyl-α-cyclodextrin.

The results show that the percentage of the glucosyl-α-cyclodextrin in the mixture containing the glucosyl-α-cyclodextrin is 10%.

Option 3: The activity of the α-CGTase in step (2) in the example 1 is reduced to 0.0006 U (i.e., to ensure that the initial activity of the α-CGTase in the subsequent reaction system is about 0.06 U/g of the mixture by dry weight); and other steps and parameters are the same as those in the example 1, specifically:

(1) putting 10 mg of maltodextrin in a 2 mL centrifuge tube, adding 1 mL of a pH 4.5 (20 mM) phosphate buffer solution, adding 0.36 U of α-CGTase, and reacting at 60° C. for 12 h to obtain a mixture containing branched cyclodextrin glucosyl-α-cyclodextrin;

(2) performing heating in water bath of 80° C. for 10 min, so as to enable the activity of the α-CGTase to be 0.0006 U (i.e., to ensure that the initial activity of the α-CGTase in the subsequent reaction system is about 0.06 U/g of the mixture by dry weight); and (3) adding 0.72 U of saccharifying enzyme to the reaction system, reacting at 45° C. for 12 h, and insulating the temperature at 100° C. for 15 min to obtain a mixture containing glucosyl-α-cyclodextrin.

The results show that the percentage of the glucosyl-α-cyclodextrin in the mixture containing the glucosyl-α-cyclodextrin is 14%.

Option 4: The activity of the α-CGTase in step (2) in the example 1 is reduced to 0 U (i.e., to ensure that the initial activity of the α-CGTase in the subsequent reaction system is about 0); and other steps and parameters are the same as those in the example 1, specifically:

(1) putting 10 mg of maltodextrin in a 2 mL centrifuge tube, adding 1 mL of a pH 4.5 (20 mM) phosphate buffer solution, adding 0.36 U of α-CGTase, and reacting at 60° C. for 12 h to obtain a mixture containing branched cyclodextrin glucosyl-α-cyclodextrin;

(2) performing heating in water bath of 80° C. for 10 min, so as to enable the activity of the α-CGTase to be 0; and (3) adding 0.72 U of saccharifying enzyme to the reaction system, reacting at 45° C. for 12 h, and insulating the temperature at 100° C. for 15 min to obtain a mixture containing glucosyl-α-cyclodextrin.

The results show that the percentage of the glucosyl-α-cyclodextrin in the mixture containing the glucosyl-α-cyclodextrin is 3.5%.

Example 3

A method for preparing glucosyl-β-cyclodextrin by enzymatically treating maltodextrin, comprising the following specific steps:

(1) putting 50 mg of maltodextrin in a 2 mL centrifuge tube, adding 1 mL of a pH 3.0 (20 mM) phosphate buffer solution, adding 0.36 U of β-CGTase, and reacting at 60° C. for 12 h;

(2) performing heating in water bath of 90° C. for 5 min, so as to enable the activity of the β-CGTase to be 0.011 U (i.e., to ensure that the initial activity of the β-CGTase in the subsequent reaction system is about 0.22 U/g of the mixture by dry weight);

(3) adding 0.72 U of saccharifying enzyme to the reaction system, reacting at 45° C. for 12 h, and insulating the temperature at 100° C. for 15 min to obtain a mixture containing glucosyl-β-cyclodextrin; and (4) separating and purifying the product obtained in step (3) by a high-performance liquid chromatography method to finally obtain 0.56 mg of glucosyl-β-cyclodextrin.

Figure 2:
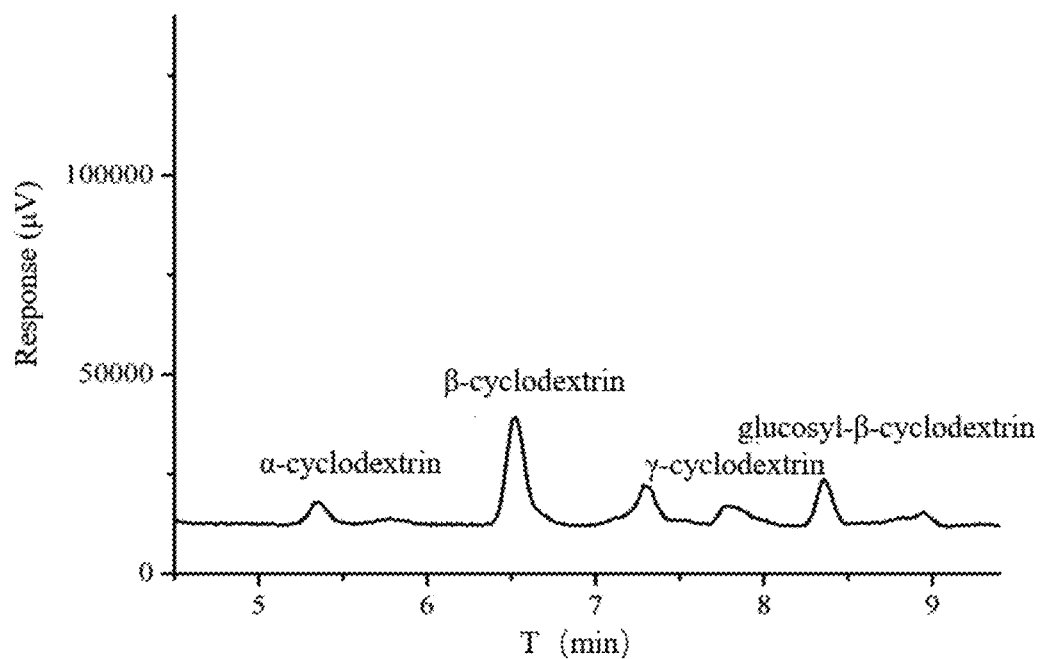
FIG. 2 is a high-performance liquid chromatogram of the product of step (3) in example 3 of the disclosure.

The samples of steps (1) and (3) in this example are subjected to high performance liquid chromatography analysis and test, and the test results are shown in FIGS. 1 and 2.

It can be seen from FIG. 1 that glucosyl-βcyclodextrin is generated by adding β-CGTase to maltodextrin as a substrate, but the yield is only 0.19 mg, which is only 2.4% of the main products (α-cyclodextrin, β-cyclodextrin, γ-cyclodextrin and glucosyl-β-cyclodextrin).

It can be seen from FIG. 2 that after adding β-CGTase to maltodextrin as a substrate, the content of the obtained glucosyl-β-cyclodextrin is 0.42 mg under the combined action of the β-CGTase and the saccharifying enzyme, and is 24.0% of the main products.

Example 4

A method for preparing glucosyl-γ-cyclodextrin by enzymatically treating maltodextrin, comprising the following specific steps:

(1) putting 50 mg of maltodextrin in a 2 mL centrifuge tube, adding 1 mL of a pH 3.0 (20 mM) phosphate buffer solution, adding 0.36 U of γ-CGTase, and reacting at 60° C. for 12 h;

(2) performing heating in water bath of 90° C. for 5 min, so as to enable the activity of the γ-CGTase to be 0.011 U;

(3) adding 0.72 U of saccharifying enzyme to the reaction system, reacting at 45° C. for 12 h, and insulating the temperature at 100° C. for 15 min to obtain a mixture containing glucosyl-γ-cyclodextrin; and (4) separating and purifying the product obtained in step (3) by a high-performance liquid chromatography method to finally obtain 0.37 mg of glucosyl-γ-cyclodextrin.

Example 5

A method for preparing single maltosyl-α-cyclodextrin by an enzyme method, comprising the following specific steps:

(1) taking 0.1 g of a mixture containing maltose, α-cyclodextrin and maltosyl-α-cyclodextrin prepared by a pullulanase reverse synthesis method, and dissolving the mixture in 300 μL of a pH 4.5 phosphate buffer solution;

(2) placing the above solution at 4° C. for crystallizing at low temperature for 12 h;

(3) centrifuging the solution obtained in step (2) at 4° C., and adding the supernatant to 600 μL of a pH 4.5 buffer solution to be fully dissolved;

(4) adding 150 μL (i.e. 0.03 U) of CGTase and 150 μL (i.e. 0.72 U) of saccharifying enzyme to the reaction system, and reacting at 45° C. for 4 h to obtain a mixture containing maltosyl-α-cyclodextrin, maltose and glucose; and (5) further separating and purifying the mixture by a membrane separation method to obtain the maltosyl-α-cyclodextrin.

The key of this part is to hydrolyze the α-cyclodextrin in the mixture into glucose to facilitate separation of maltosyl-α-cyclodextrin, because the molecular weight of α-cyclodextrin and maltosyl-α-cyclodextrin differs by 342, which is disadvantageous for molecules (the molecular weight is approximate), and the molecular weight of glucose and maltosyl-α-cyclodextrin differs by 972. The principle of a separation method of such substances is generally based on the size of the substances, and the larger the difference between the two substances, the easier it is to separate, and vice versa.

Example 6

A method for preparing single maltosyl-β-cyclodextrin by an enzyme method, comprising the following specific steps:

(1) taking 0.1 g of a mixture containing maltose, β-cyclodextrin and maltosyl-β-cyclodextrin prepared by a pullulanase reverse synthesis method, and dissolving the mixture in 300 μL of a pH 4.5 phosphate buffer solution;

(2) placing the above solution at 4° C. for crystallizing at low temperature for 12 h;

(3) centrifuging the solution obtained in step (2) at 4° C., and adding the supernatant to 600 μL of a pH 4.5 buffer solution to be fully dissolved;

(4) adding 150 μL (i.e. 0.03 U) of CGTase and 150 μL (i.e. 0.72 U) of saccharifying enzyme to the reaction system, and reacting at 45° C. for 4 h to obtain a mixture containing maltosyl-β-cyclodextrin, maltose and glucose; and (5) further separating and purifying the mixture by a membrane separation method to obtain the maltosyl-β-cyclodextrin.

Figure 3:
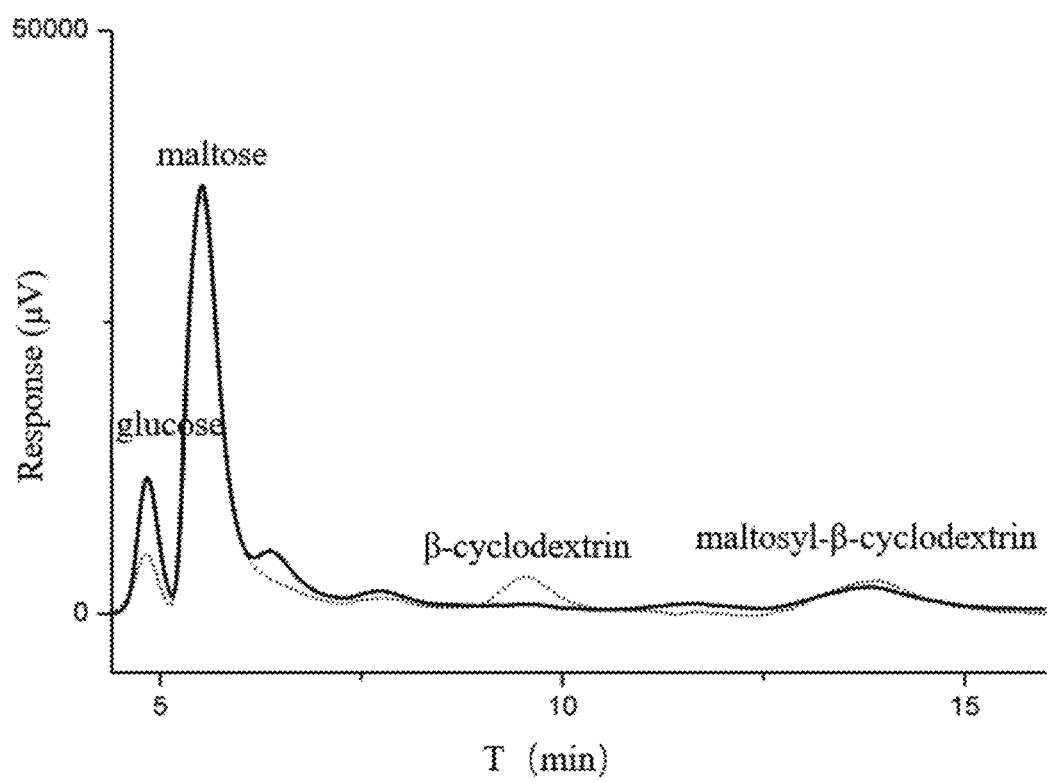
FIG. 3 is a high-performance liquid chromatogram of the products of steps (3) and (4) in example 6 of the disclosure.

The products of steps (3) and (4) in this example of the disclosure are analyzed and tested by high performance liquid chromatography, and the test results are shown in FIG. 3, wherein the dotted line represents the sample before enzyme treatment, and the solid line represents the sample after the enzyme treatment. It can be seen from FIG. 3 that in a mixture containing maltose, β-cyclodextrin and maltosyl-β-cyclodextrin prepared by the pullulanase reverse synthesis method, the β-cyclodextrin is hydrolyzed under the combined action of the CGTase and the saccharifying enzyme, finally a mixture containing maltosyl-β-cyclodextrin, maltose and glucose can be obtained, and the maltosyl-β-cyclodextrin can be obtained by a membrane separation method.

Example 7

A method for preparing single maltosyl-γ-cyclodextrin by an enzyme method, comprising the following specific steps:

(1) taking 0.1 g of a mixture containing maltose, γ-cyclodextrin and maltosyl-γ-cyclodextrin prepared by a pullulanase reverse synthesis method, and dissolving the mixture in 300 μL of a pH 4.5 phosphate buffer solution;

(2) placing the above solution at 4° C. for crystallizing at low temperature for 12 h;

(3) centrifuging the solution obtained in step (2) at 4° C., and adding the supernatant to 600 μL of a pH 4.5 buffer solution to be fully dissolved;

(4) adding 150 μL (i.e. 0.03 U/g mixture) of CGTase and 150 μL (i.e. 0.72 U/g mixture) of saccharifying enzyme to the reaction system, and reacting at 45° C. for 4 h to obtain a mixture containing maltosyl-γ-cyclodextrin, maltose and glucose; and (5) further separating and purifying the mixture by a membrane separation method to obtain the maltosyl-γ-cyclodextrin.

Example 8

A method for preparing single galactosyl-β-cyclodextrin by an enzyme method, comprising the following specific steps:

(1) taking 0.1 g of a mixture containing melibiose, β-cyclodextrin and galactosyl-β-cyclodextrin prepared by an α-galactosidase synthesis method, and dissolving the mixture in 300 μL of a pH 4.5 phosphate buffer solution;

(2) placing the above solution at 4° C. for crystallizing at low temperature for 12 h;

(3) centrifuging the solution obtained in step (2) at 4° C., and adding the supernatant to 600 μL of a pH 4.5 buffer solution to be fully dissolved;

(4) adding 150 μL (i.e. 0.03 U/g mixture) of CGTase and 150 μL (i.e. 0.72 U/g mixture) of saccharifying enzyme to the reaction system, and reacting at 45° C. for 4 h to obtain a mixture containing galactosyl-β-cyclodextrin, melibioze and glucose; and (5) further separating and purifying the mixture by a membrane separation method to obtain the galactosyl-β-cyclodextrin.

Example 9

A method for preparing single glucosyl-β-cyclodextrin by an enzyme method, comprising the following specific steps:

(1) taking 0.1 g of a mixture containing maltose, β-cyclodextrin and maltosyl-β-cyclodextrin prepared by a pullulanase reverse synthesis method, and dissolving the mixture in 300 μL of a pH 4.5 phosphate buffer solution;

(2) placing the above solution at 4° C. for crystallizing at low temperature for 12 h;

(3) centrifuging the solution obtained in step (2) at 4° C., and adding the supernatant to 600 μL of a pH 4.5 buffer solution to be fully dissolved;

(4) adding 100 μL (i.e. 0.72 U) of saccharifying enzyme to the reactant liquor, reacting at 45° C. for 10 h and insulating the temperature at 100° C. for 15 min to obtain a mixture containing maltose, glucose, β-cyclodextrin and glucosyl-β-cyclodextrin;

(5) adding 150 μL of CGTase (i.e. the amount of the CGTase in a control system is 0.03 U/g mixture) and 150 μL (i.e. 0.72 U/g mixture) of saccharifying enzyme to the reaction system, and reacting at 45° C. for 4 h to obtain a mixture containing glucosyl-β-cyclodextrin, glucose and maltose; and (6) further separating and purifying the mixture by a membrane separation method to obtain the glucosyl-β-cyclodextrin.

Figure 4:
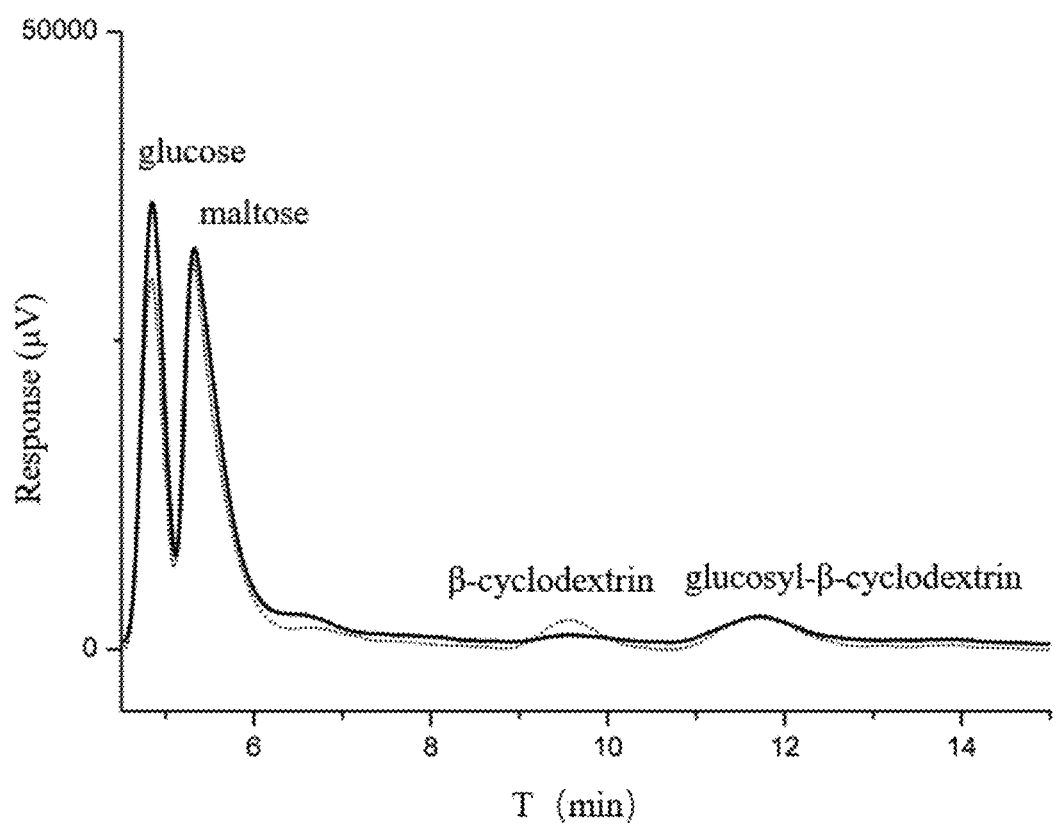
FIG. 4 is a high-performance liquid chromatogram of the products of steps (4) and (5) in example 9 of the disclosure.

The products of steps (4) and (5) in this example of the disclosure are analyzed and tested by high performance liquid chromatography, and the test results are shown in FIG. 4, wherein the dotted line represents the sample before enzyme treatment, and the solid line represents the sample after the enzyme treatment. It can be seen from FIG. 4 that a mixture containing maltose, β-cyclodextrin and maltosyl-β-cyclodextrin prepared by a pullulanase reverse synthesis method is prepared into a mixture of maltose, glucose, 3-cyclodextrin and glucosyl-β-cyclodextrin under the action of the saccharifying enzyme; the 3-cyclodextrin can be hydrolyzed under the combined action of the CGTase and the saccharifying enzyme, finally a mixture containing glucosyl-β-cyclodextrin, maltose and glucose can be obtained, and the glucosyl-β-cyclodextrin can be obtained by a membrane separation method.

What is claimed is:

1. A method for preparing branched cyclodextrin, comprising: incubating a branched cyclodextrin-containing mixture with 0.1 to 0.4 U/g by dry weight cyclodextrin glucosyltransferase (CGTase) and a saccharifying enzyme for 12 to 24 hours, wherein the saccharifying enzyme is glucoamylase.

2. The method according to claim 1, wherein the branched cyclodextrin-containing mixture is obtained by incubating maltodextrin with CGTase, or by a pullulanase reverse synthesis method, or by incubating α-galactosidase with cyclodextrin and melibiose.

3. The method according to claim 1, wherein the branched cyclodextrin-containing mixture is obtained by first dissolving maltodextrin in a buffer solution, and then incubating with the CGTase 12 to 24 hours.

4. The method according to claim 3, wherein after the maltodextrin is dissolved in the buffer solution, obtaining a solution with mass concentration of the maltodextrin of 1% to 5%.

5. The method according to claim 1, comprising:
dissolving maltodextrin in a phosphate buffer solution, adding the CGTase and reacting for 12 to 24 hours to obtain the branched cyclodextrin-containing mixture;
reducing CGTase activity by a physical method; and
adding the saccharifying enzyme, reacting for 12 to 24 hours, and
performing high-temperature enzyme deactivation to obtain branched cyclodextrin.

6. The method according to claim 1, wherein the method further comprises separating and purifying a reaction product.

7. The method according to claim 1, wherein the CGTase is any one or more of α-CGTase, β-CGTase and γ-CGTase.

8. The method according to claim 7, comprising:
providing 10 mg of maltodextrin and 1 mL of a pH 4.5 (20 mM) phosphate buffer solution, adding 0.36 U of α-CGTase, and reacting at 60° C. for 12 hours;
heating the maltodextrin in a water bath at 80° C. for 10 minutes;
adding 0.72 U of saccharifying enzyme, reacting at 45° C. for 12 hours, and maintaining temperature at 100° C. for 15 minutes; and
separating and purifying the product by a high-performance liquid chromatography method to obtain glucosyl-α-cyclodextrin.

9. The method according to claim 7, comprising:
providing 50 mg of maltodextrin and 1 mL of a pH 3.0 (20 mM) phosphate buffer solution, adding 0.36 U of β-CGTase, and reacting at 60° C. for 12 hours;
heating the maltodextrin in a water bath at 90° C. for 5 minutes;
adding 0.72 U of saccharifying enzyme and incubating at 45° C. for 12 hours, and maintaining temperature at 100° C. for 15 min; and
separating and purifying the product by a high-performance liquid chromatography method to obtain glucosyl-β-cyclodextrin.

10. The method according to claim 7, comprising:
providing 50 mg of maltodextrin and 1 mL of a pH 3.0 (20 mM) phosphate buffer solution, adding 0.36 U of γ-CGTase, and reacting at 60° C. for 12 hours;
heating in a water bath at 90° C. for 5 minutes;
adding 0.72 U of saccharifying enzyme, reacting at 45° C. for 12 hours, and maintaining temperature at 100° C. for 15 min; and
separating and purifying the product by a high-performance liquid chromatography method to obtain glucosyl-γ-cyclodextrin.

11. The method of claim 1, wherein the cyclodextrin glucosyltransferase (CGTase) is present in an amount of 0.2 to 0.3 U/g.

12. The method according to claim 2, comprising:
(a) dissolving a powdered branched cyclodextrin-containing mixture prepared by the pullulanase reverse synthesis method in a buffer solution;
(b) crystallizing the buffer solution obtained in step (a) at 0° C. to 20° C. for 12 to 24 hours;
(c) centrifuging the solution obtained in step (b) to obtain a supernatant, and adding the supernatant to a buffer solution of pH 4.5 to 8.0; and
(d) adding CGTase and the saccharifying enzyme, and reacting at 45° C.

13. The method according to claim 2, further comprising separating and purifying the reaction product by a membrane separation method to obtain single branched cyclodextrin.

14. A method for preparing branched cyclodextrin, comprising: incubating a branched cyclodextrin-containing mixture with between 0.3 U/g and 1.1 U/g by dry weight cyclodextrin glucosyltransferase (CGTase) and a saccharifying enzyme for 12 to 24 hours, wherein the saccharifying enzyme is glucoamylase.

* * * * *